US009119737B2

(12) United States Patent
Mertens et al.

(10) Patent No.: US 9,119,737 B2
(45) Date of Patent: *Sep. 1, 2015

(54) TWISTING BIFURCATION DELIVERY SYSTEM

(75) Inventors: Steven P. Mertens, New Hope, MN (US); David Elizondo, Champlin, MN (US); Andrzej Malewicz, Minneapolis, MN (US); Matt Heidner, Maple Grove, MN (US); Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/480,748

(22) Filed: May 25, 2012

(65) Prior Publication Data
US 2012/0239129 A1 Sep. 20, 2012

Related U.S. Application Data

(63) Continuation of application No. 11/272,886, filed on Nov. 14, 2005, now Pat. No. 8,192,477.

(51) Int. Cl.
| | |
|---|---|
| A61F 2/06 | (2013.01) |
| A61F 2/954 | (2013.01) |
| A61F 2/958 | (2013.01) |
| A61M 25/04 | (2006.01) |
| A61M 25/00 | (2006.01) |
| A61M 29/02 | (2006.01) |

(52) U.S. Cl.
CPC .............. *A61F 2/954* (2013.01); *A61F 2/958* (2013.01); *A61M 25/04* (2013.01); *A61F 2002/061* (2013.01); *A61F 2002/065* (2013.01); *A61M 2025/0058* (2013.01); *A61M 2029/025* (2013.01)

(58) Field of Classification Search
CPC ... A61F 2/954; A61F 2/958; A61F 2002/061; A61F 2002/065; A61M 25/04; A61M 2025/0058; A61M 2029/025
USPC .................. 606/108; 623/1.23, 1.35, 1.37
See application file for complete search history.

(56) References Cited

U.S. PATENT DOCUMENTS

| | | | |
|---|---|---|---|
| 4,576,142 A | 3/1986 | Schiff | |
| 5,037,392 A * | 8/1991 | Hillstead | 606/194 |
| 5,078,727 A | 1/1992 | Hannam et al. | |
| 5,146,925 A | 9/1992 | Snow | |
| 5,163,928 A | 11/1992 | Hobbs et al. | |
| 5,290,230 A | 3/1994 | Ainsworth et al. | |
| 5,338,295 A | 8/1994 | Cornelius et al. | |
| 5,409,458 A | 4/1995 | Khairkhahan et al. | |

(Continued)

FOREIGN PATENT DOCUMENTS

| | | |
|---|---|---|
| EP | 0 897 700 | 2/1999 |
| GB | 3531 | 0/1913 |

(Continued)

*Primary Examiner* — David Eastwood
(74) *Attorney, Agent, or Firm* — Seager, Tufte & Wickhem LLP

(57) ABSTRACT

A catheter system comprises a catheter having an elongate catheter shaft such that a portion of the catheter shaft proximal a stent retaining region defines at least one bend that is bent around the longitudinal axis of a vessel. The catheter also has a side branch guidewire housing, defining a side branch guidewire lumen, and a side branch guidewire that extends through the side branch guidewire lumen.

18 Claims, 19 Drawing Sheets

(56) References Cited

U.S. PATENT DOCUMENTS

| | | |
|---|---|---|
| 5,489,271 A | 2/1996 | Andersen |
| 5,545,132 A | 8/1996 | Fagan et al. |
| 5,743,875 A | 4/1998 | Sirhan et al. |
| 5,749,825 A | 5/1998 | Fischell et al. |
| 5,873,865 A | 2/1999 | Horzewski et al. |
| 6,059,823 A | 5/2000 | Holman et al. |
| 6,096,073 A | 8/2000 | Webster et al. |
| 6,099,497 A * | 8/2000 | Adams et al. ............. 604/96.01 |
| 6,117,117 A | 9/2000 | Mauch |
| 6,174,327 B1 | 1/2001 | Mertens et al. |
| 6,475,208 B2 * | 11/2002 | Mauch ........................ 604/510 |
| 6,544,218 B1 | 4/2003 | Choi |
| 6,596,020 B2 | 7/2003 | Vardi et al. |
| 6,607,534 B2 | 8/2003 | Bonutti |
| 6,679,860 B2 | 1/2004 | Stiger |
| 6,692,483 B2 * | 2/2004 | Vardi et al. .................... 604/529 |
| 6,706,062 B2 | 3/2004 | Vardi et al. |
| 6,709,429 B1 | 3/2004 | Schaefer et al. |
| 6,749,628 B1 | 6/2004 | Callol et al. |
| 8,192,477 B2 * | 6/2012 | Mertens et al. .............. 623/1.11 |
| 2001/0003161 A1 | 6/2001 | Vardi et al. |
| 2001/0007082 A1 | 7/2001 | Dusbabek et al. |
| 2001/0039448 A1 * | 11/2001 | Dibie .......................... 623/1.16 |
| 2002/0183763 A1 * | 12/2002 | Callol et al. .................. 606/108 |
| 2003/0055483 A1 | 3/2003 | Gumm |
| 2003/0181923 A1 | 9/2003 | Vardi |
| 2004/0039326 A1 | 2/2004 | Hata et al. |
| 2004/0073286 A1 | 4/2004 | Armstrong et al. |
| 2004/0097965 A1 | 5/2004 | Gardeski et al. |
| 2004/0102719 A1 | 5/2004 | Keith et al. |
| 2004/0172119 A1 | 9/2004 | Eidenschink |
| 2004/0172121 A1 * | 9/2004 | Eidenschink et al. ....... 623/1.11 |
| 2004/0186508 A1 * | 9/2004 | Adams et al. ................. 606/194 |
| 2004/0220606 A1 | 11/2004 | Goshgarian |
| 2005/0015108 A1 | 1/2005 | Williams et al. |
| 2006/0058864 A1 | 3/2006 | Schaeffer et al. |
| 2006/0100694 A1 * | 5/2006 | Globerman .................. 623/1.35 |
| 2009/0287148 A1 * | 11/2009 | Martin et al. ............ 604/101.01 |

FOREIGN PATENT DOCUMENTS

| | | |
|---|---|---|
| WO | 93/13827 | 7/1993 |
| WO | WO 9915103 A1 * | 4/1999 |

* cited by examiner

TWISTING BIFURCATION DELIVERY SYSTEM

CROSS-REFERENCE TO RELATED APPLICATIONS

This application is a continuation of co-pending U.S. application Ser. No. 11/272,886, filed Nov. 14, 2005, the entire disclosure of which is incorporated herein by reference.

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Stents may be delivered using suitable delivery systems. For example, a stent may be oriented about an inflation balloon of a delivery catheter. The catheter may be maneuvered through a bodily vessel to deliver the stent to a deployment site. The stent may be expanded by inflating the balloon with an inflation medium, such as a pressurized fluid. The balloon may then be deflated, and the catheter removed from the body.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention contemplates new and improved apparatuses that simplify placement of a stent at the site of a vessel bifurcation. Embodiments of the present invention include systems that provide improved trackability during delivery as well as accuracy of delivery.

It is understood that the term "shaft" includes the inner shaft, the outer shaft, or a combination of the inner shaft and outer shaft.

In at least one embodiment, the invention is directed to a catheter having an elongate catheter shaft with a distal region and a proximal region. The distal region of the catheter shaft defines a stent retaining region. Proximal to the stent retaining region, the catheter shaft defines at least one bend such that the bend is bent around the longitudinal axis of the vessel. The catheter also has a side branch guidewire housing which defines a side branch guidewire lumen; a side branch guidewire extends through the side branch guidewire lumen.

In some embodiments the catheter shaft proximal to the stent retaining region has plurality of bends such that the catheter shaft has a helical shape. That is, each bend, disposed about the longitudinal axis of the vessel, is joined to form a first helical path. In other embodiments, the path may be spiral rather than helical.

In at least one embodiment, the side branch guidewire is bent about the longitudinal axis of the vessel and is disposed about the catheter shaft.

In some embodiments, at least a portion of the catheter shaft is comprised of a braided material.

In other embodiments, the catheter shaft further defines an exchange port immediately proximally adjacent to a bend. The catheter shaft has a primary guidewire lumen and a primary guidewire which extends through the exchange port and the primary guidewire lumen. The exchange port is in communication with the primary guidewire lumen.

In at least one embodiment, the catheter also comprises an expandable balloon with a first length and a side branch guidewire housing with a second length wherein the second length is equal to or greater than the first length.

The trackability of a catheter through a vessel may be improved by improving the ability of the catheter to bend around the guidewires. By employing side branch guidewire housings of specific shapes, torque transfer may be improved over current methods.

In at least one embodiment, the cross-sectional width of the side branch guidewire housing is greater than the cross-sectional height.

In some embodiments, the side branch guidewire housing has a substantially elliptical cross-sectional shape.

In at least one embodiment, the cross-sectional shape of the side branch guidewire housing has a plurality of peaks and troughs wherein each peak is separated by a trough. The peaks are at a greater radial distance from the longitudinal axis of the catheter shaft than the troughs. In some embodiments, the troughs are substantially curvilinear.

The accuracy of the stent placement at a vessel bifurcation is critical. If the stent is not accurately placed, it is possible that the stent will be deployed too close to either the carina or contralateral wall of the vessel side branch, thereby causing a stenosis to form. The stenosis may grow into the stent and result in stent occlusion.

In some embodiments, at least a portion of the side branch guidewire housing extends at an oblique angle away from the expandable balloon. Disposed about the oblique-angled portion of the side branch guidewire housing is an expandable centering band which, in some embodiments, defines a centering band inflation lumen. The expandable centering band has an expanded state and an unexpanded state and, in embodiments with a centering band inflation lumen, is in fluid communication with the centering band inflation lumen. Adapted to receive an inflation fluid, the centering band is substantially filled with inflation fluid in the expanded state, and is substantially free of inflation fluid and substantially ring-shaped in the unexpanded state.

In at least one embodiment, the centering band is substantially conical in the expanded state. Specifically, the centering band has a vertex and a base wherein the vertex has a diameter less than that of the base, and the vertex is closer to the expandable balloon than the base. In other embodiments, the base is closer to the expandable balloon than the vertex.

The trackability of a catheter system may be improved by altering the flexibility characteristics of the catheter shaft. By making the catheter shaft more flexible in some regions than in other regions, the catheter system may be advanced through the vasculature with less difficulty, thereby potentially reducing damage to the vessel walls as well as increasing delivery accuracy. Furthermore, altering the shape of the catheter shaft may produce similar desirable effects.

In at least one embodiment, a portion of the catheter shaft comprises a flexible, pleated region. In some embodiments the flexible, pleated region extends around the entire circumference of a portion of the catheter shaft. In other embodiments the flexible, pleated region is disposed about only a section of the circumference of the portion of the catheter shaft.

In at least one embodiment, the catheter shaft has a cross-section and comprises a body with an interior, exterior, and a longitudinal axis. The exterior has a plurality of peaks and troughs, each peak being separated by a trough. The peaks are at a greater radial distance from the longitudinal axis of the catheter shaft than the troughs. In some embodiments, the interior defines a substantially circular region. In other embodiments, the troughs are substantially curvilinear.

In at least one embodiment, the interior, like the exterior, comprises a plurality of peaks and troughs, each peak being separated by a trough. The peaks are at a greater radial distance from the longitudinal axis of the catheter shaft than the troughs. The peaks of the interior radially correspond to the peaks of the exterior and the troughs of the interior radially correspond to the troughs of the exterior. In some embodiments, at least a portion of at least one peak comprises a support. The support, substantially parallel to the longitudinal axis of the body, extends through the peak.

In at least one embodiment, the body is comprised of a first material and the support is comprised of a second material, the first material being different from the second material. In some embodiments the first material is more flexible than the second material. In other embodiments the first material is less flexible than the second material.

In some embodiments the cross-section of the catheter shaft is substantially triangular.

The trackability of a catheter system may also be improved by altering the push characteristics of the catheter shaft. Being able to change the longitudinal stiffness, that is, the push characteristics, of the catheter shaft, the catheter system may be advanced through the vasculature with less difficulty, thereby potentially reducing damage to the vessel walls as well as increasing delivery accuracy.

For example, in at least one embodiment the invention is directed to a catheter having an elongate catheter shaft with a distal region and a proximal region. The catheter shaft comprises a substantially tubular wall and defines an inflation lumen. The distal region of the catheter shaft defines a stent retaining region. Proximal to the stent retaining region, the catheter shaft defines at least one bend such that the bend is bent around the longitudinal axis of the vessel. The catheter also has a side branch guidewire housing which defines a side branch guidewire lumen; a side branch guidewire extends through the side branch guidewire lumen. Furthermore, the catheter system comprises at least one support member having a first portion and a second portion such that the first portion is more flexible than the second portion.

In some embodiments the first portion comprises at least one flexible, pleated region. In other embodiments, the support member is wire. In at least one embodiment, the support member is a polymer. In at least one embodiment the support member extends through at least a portion of the inflation lumen. In some embodiments, the support member extends through at least a portion of the tubular wall.

Push characteristics may be altered by using varied inflation methods and/or mechanisms within the catheter shaft. For example, in at least one embodiment of the invention the catheter shaft comprises a substantially tubular wall having an inner diameter defining a first inflation lumen for balloon inflation. A second inflation lumen, capable of altering the push characteristics, extends longitudinally through at least a portion of the tubular wall. The second inflation lumen is capable of being inflated independent of the first inflation lumen.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
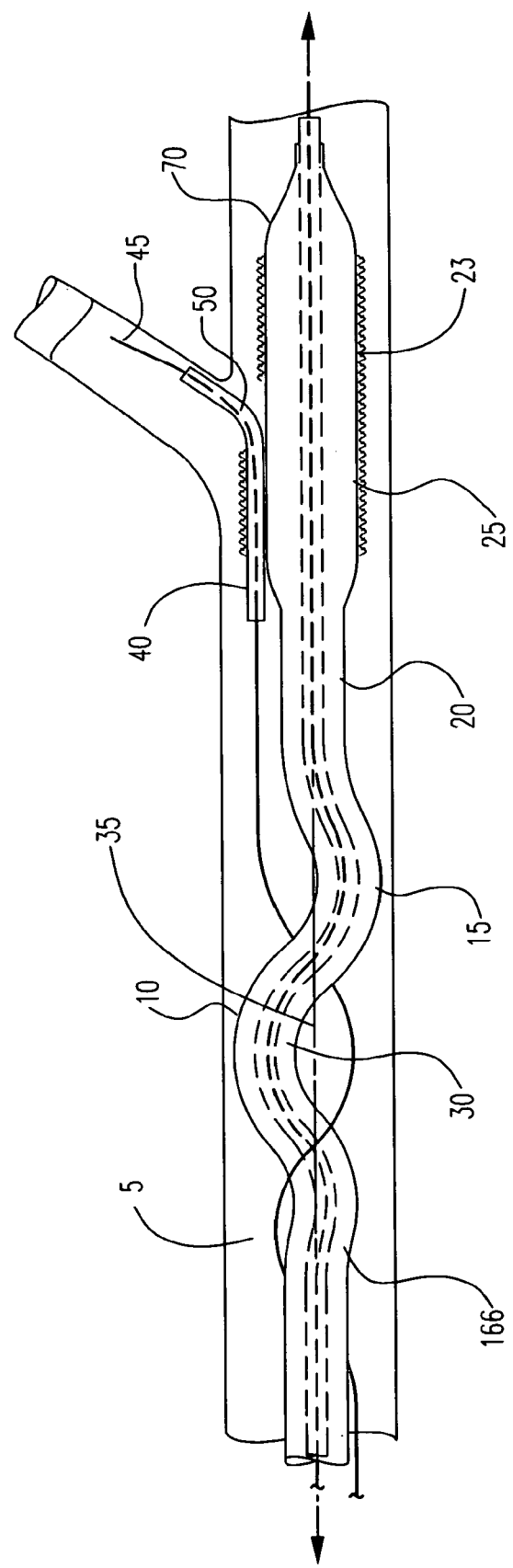
FIG. 1 is a side view of a catheter system with a portion of the catheter shaft bent around a longitudinal axis.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, and/or substituted for, elements depicted in another figure as desired.

FIG. 1 shows an embodiment of the invention, a catheter system shown generally at 5. Catheter system 5 is comprised of a catheter 10, catheter shaft 15, expandable balloon 70, side branch guidewire housing 40, and side branch guidewire 45 which extends through side branch guidewire lumen 50. The distal region 20 of catheter shaft 15 defines a stent retaining region 25 for stent 23. Proximally adjacent to the stent retaining region 25, catheter shaft 15 includes at least one bend 30, bent about a longitudinal axis 35. The catheter shaft 15 may define a helical path once bent around the longitudinal axis 35, or it may define any other substantially spiral path.

Aligning a stent with the side branch of a vessel bifurcation is a difficult task and is achieved by allowing the catheter system to rotate into place via guidewires. A side branch guidewire 45 and a primary guidewire 166 are spaced sufficiently apart, as is known in art, in order to define a path by which a catheter system 5 can track. As catheter system 5 tracks along the two guidewires (45 and 166), it will twist and/or rotate as a result of the torque created by the guidewire location. Side branch guidewire 45 is bent about longitudinal axis 35 and is disposed about the catheter shaft 15. This configuration allows at least side branch guidewire 45 and primary guidewire 166 to cross the catheter shaft 15 multiple times without becoming entangled, a common problem that results when twisting a guidewire to align a catheter system.

Figure 2:
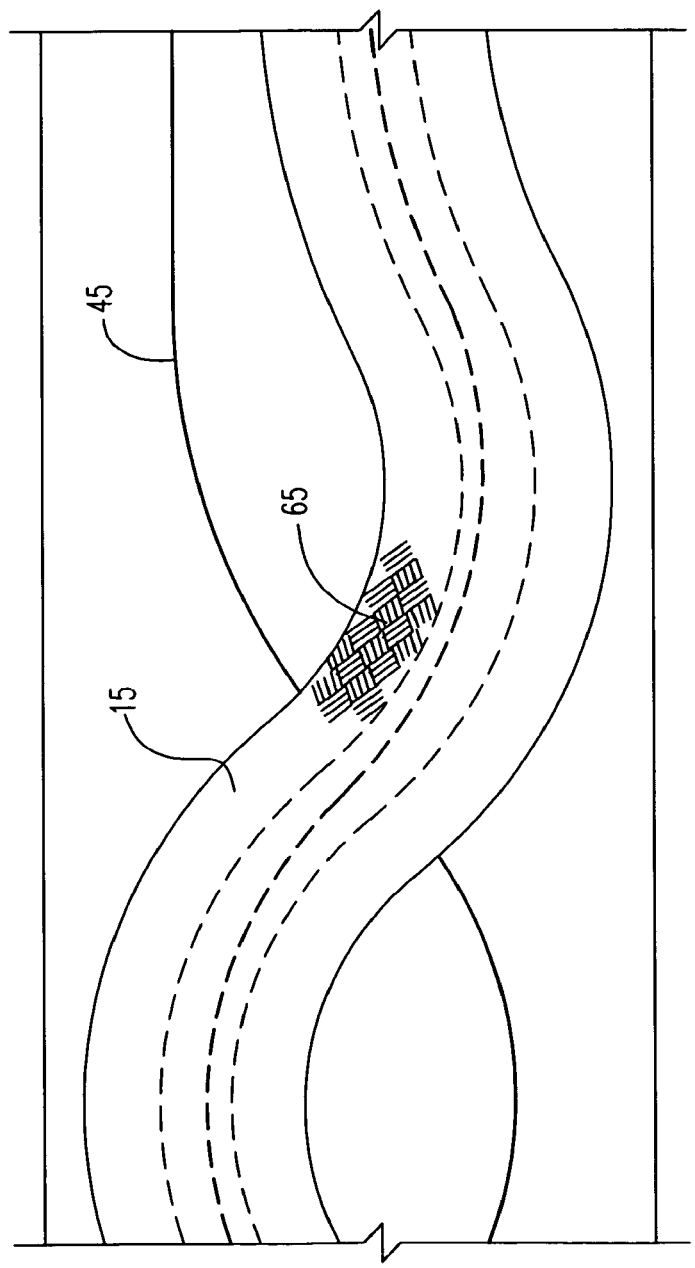
FIG. 2 is a side view of the catheter system of FIG. 1 wherein the catheter shaft is comprised of a braided material.

Because catheter shaft 15 needs to be able to twist under low loads, it may be constructed of a flexible material. Although a soft durometer material is preferable, a braided material 65, as shown in FIG. 2 can be used. Material 65 may include a braid of multiple materials having similar or different hardness, stiffness, or other material characteristics as may be desired. In at least one embodiment the braided material may comprise a pattern of material or materials interwoven, an example of which being depicted in the embodiment of FIG. 2. The braided material may be made of nylon, Pebax®, or urethane, for example. Also, a patterned catheter shaft may be used to provide the flexibility needed to achieve adequate twisting.

Figure 3:
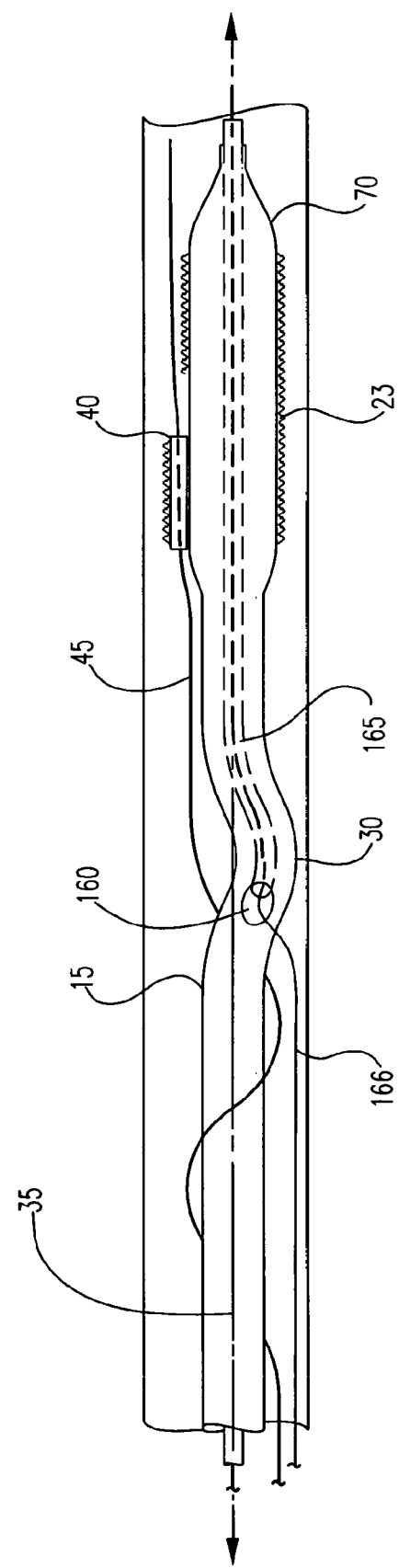
FIG. 3 is a side view of the catheter system of FIG. 1 with an exchange port.

FIG. 3 depicts another embodiment of the invention. In this embodiment, catheter system 15 includes an exchange port 160 immediately proximal to the at least one bend 30. The catheter shaft further comprises a primary guidewire lumen 165, in communication with exchange port 160, and a primary guidewire 166, extending through the exchange port 160 and the primary guidewire lumen 165. Because primary guidewire 166 does not extend through the entire catheter shaft 15, but instead enters the catheter shaft 15 at the exchange port 160, drag may be reduced, thus improving delivery performance. It should be noted that the invention may be embodied in fixed wire devices, over-the-wire devices, rapid exchange devices, MONORAIL® devices, as well as other devices that are known and used by others of ordinary skill in the art.

Figure 4:
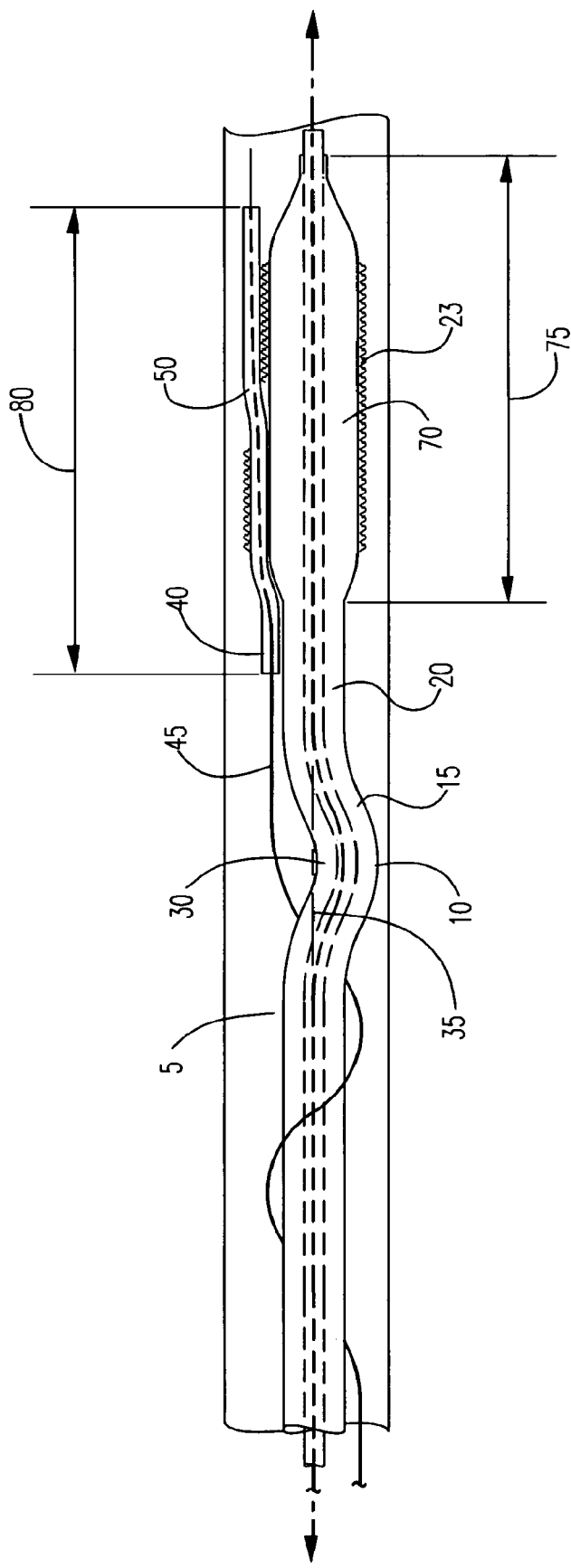
FIG. 4 is a side view of the catheter system of FIG. 1 comprising a side branch guidewire housing with a length longer than the length of the expandable balloon.

A technique of improving flexibility, which may improve trackability, is to provide a catheter system with a long side branch guidewire housing. Relative to a short side branch guidewire housing, a long side branch guidewire housing will have more flexibility at the distal end of the guidewire housing. FIG. 4 shows a catheter system 5 with side branch guidewire housing 40 and expandable balloon 70. The length 80 of side branch guidewire housing 40 is greater than the length 75 of expandable balloon 70. This increased flexibility may reduce the amount of torque required to deploy a portion of the catheter system into the side vessel, thereby simplifying delivery and deployment.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

Figure 5:
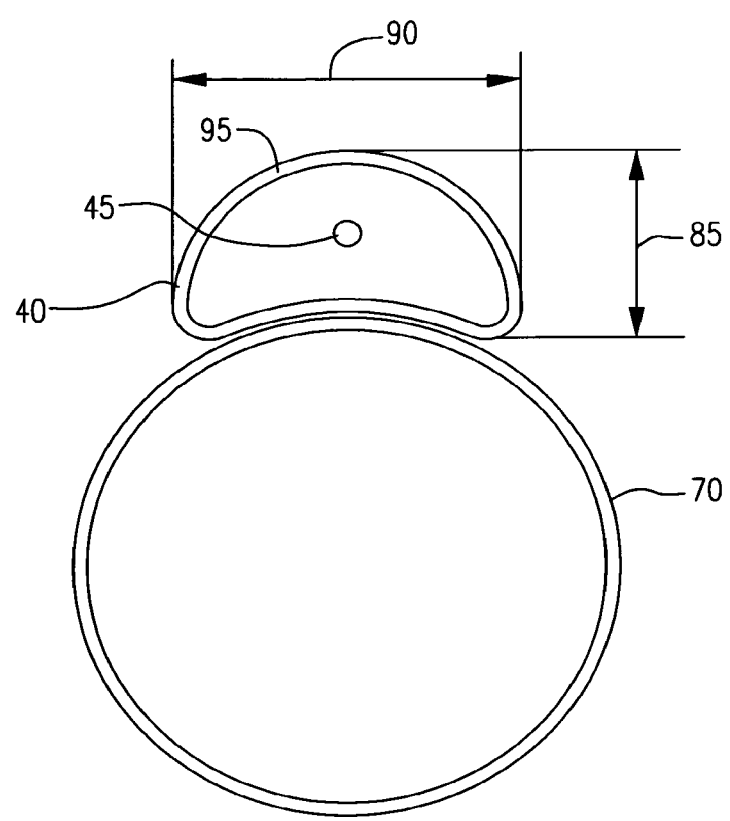
FIG. 5 is a cross-sectional view of an expandable balloon and side branch guidewire housing.
Figure 6:
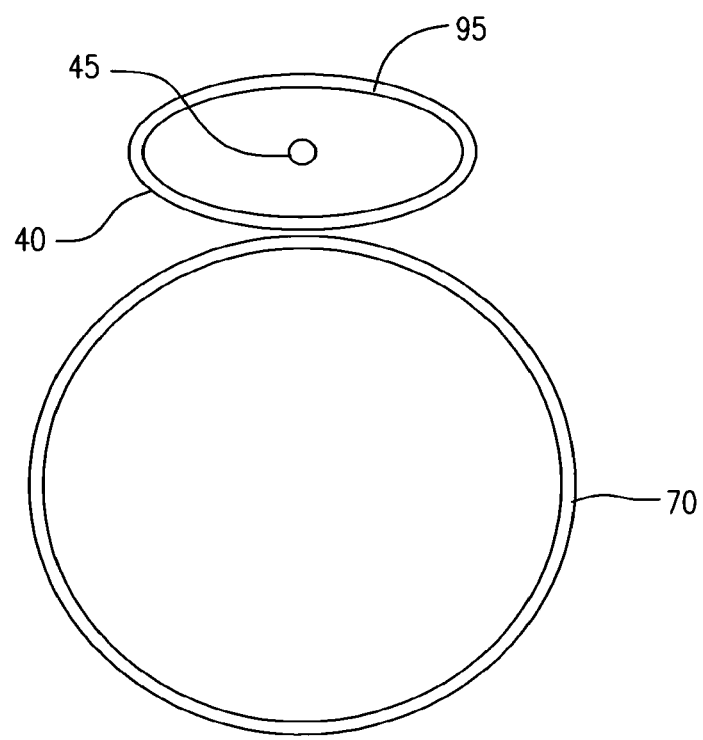
FIG. 6 is a cross-sectional view of an expandable balloon and side branch guidewire housing.
Figure 7:
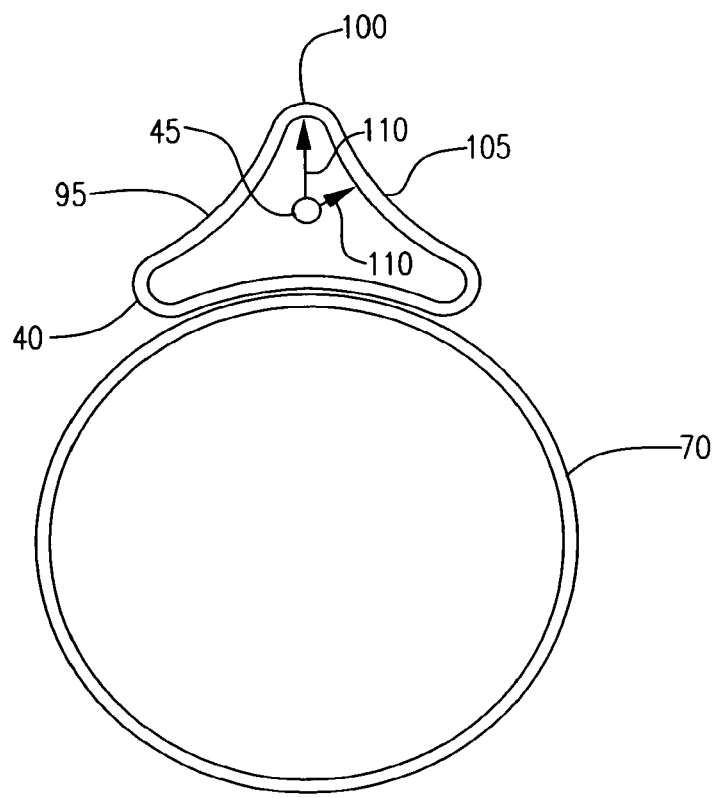
FIG. 7 is a cross-sectional view of an expandable balloon and side branch guidewire housing.

Another aspect of the invention is shown in FIGS. 5-7. Torque transfer, and therefore alignment, may be improved by altering the shape of the side branch guidewire housing 40. FIG. 5 depicts a side branch guidewire housing cross-sectional shape 95 with a width 90 greater than a height 85. FIG. 6 shows a substantially elliptical side branch guidewire housing cross-sectional shape 95. The side branch guidewire housing 40 depicted in FIG. 7 has a cross-sectional shape comprising a plurality of peaks 100 and troughs 105. Peaks 100 are at a greater radial distance 110 from the longitudinal axis 35 of the catheter shaft than the troughs 105. Each peak is separated by a trough. In some embodiments of the invention, the troughs 105 are substantially curvilinear.

Figure 8:
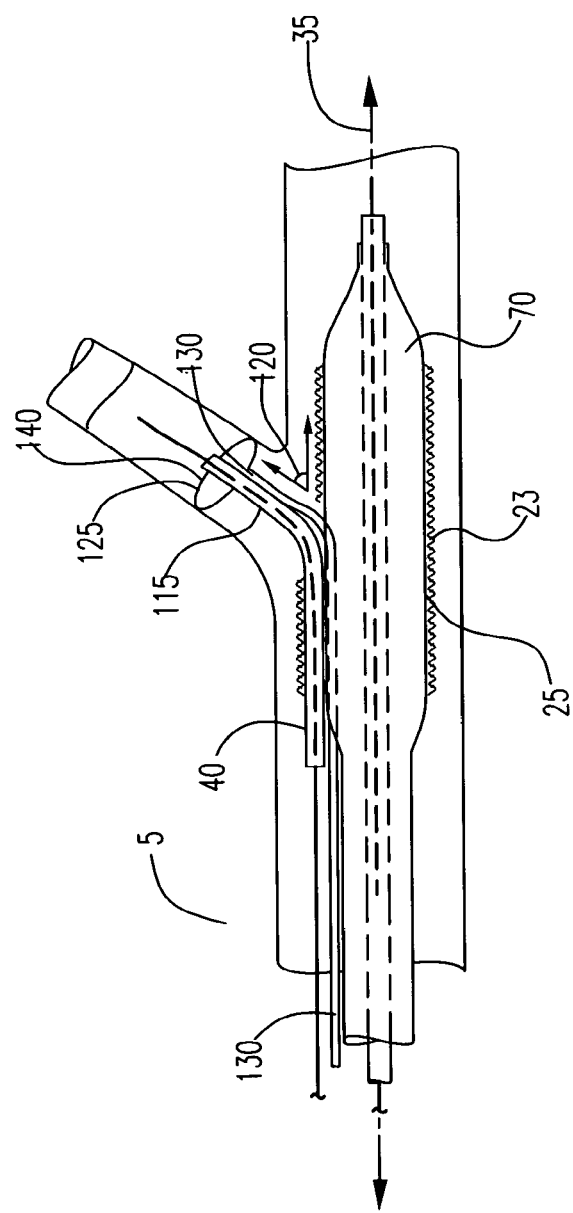
FIG. 8 is a side view of a catheter system with a centering band disposed about a portion of the side branch guidewire housing.
Figure 9:
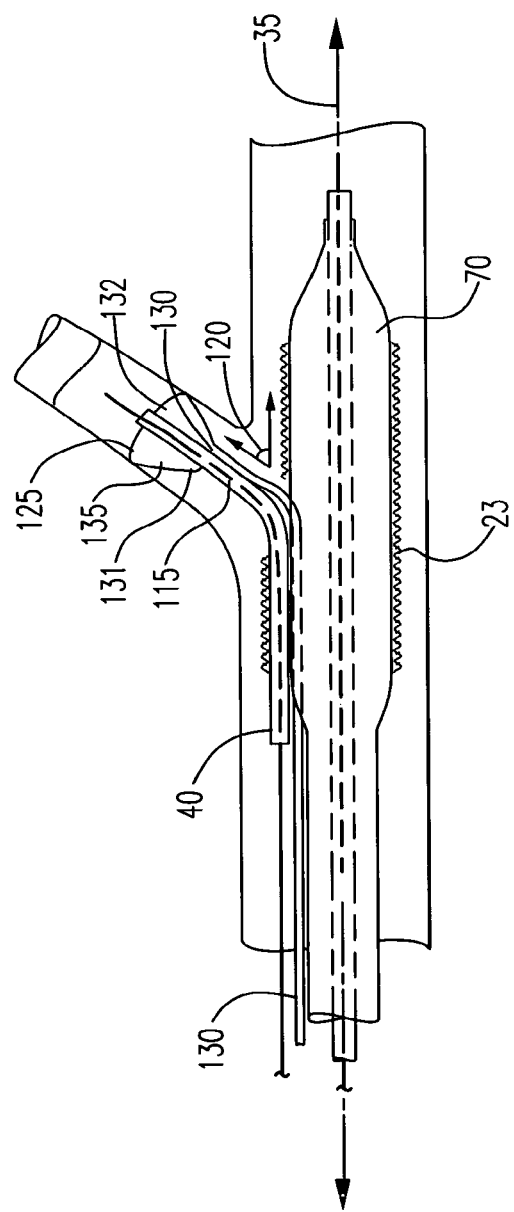
FIG. 9 is a side view of a catheter system with a centering band disposed about a portion of the side branch guidewire housing.
Figure 10:
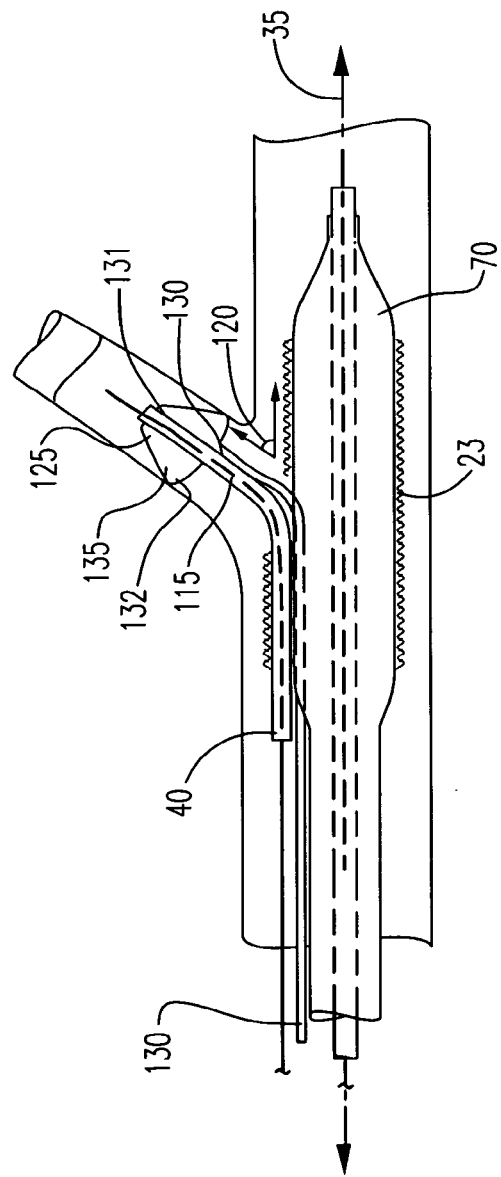
FIG. 10 is a side view of a catheter system with a centering band disposed about a portion of the side branch guidewire housing.

In some embodiments of the invention, an expandable centering band 125 is provided, as depicted in FIG. 8. The catheter system 5 of FIG. 8 includes a side branch guidewire housing 40, a portion 115 of which extends at an oblique angle 120 away from the expandable balloon 70. In fluid communication with the centering band 125 is a centering band inflation lumen 130. The centering band 125 has an expanded state and an unexpanded state such that the centering band 125 is substantially filled with inflation fluid (not shown) in the expanded state, and is substantially free of inflation fluid and substantially ring-shaped in the unexpanded state. One embodiment of the unexpanded state 140 is shown in FIG. 8. Inflation of the centering band 125 allows for guidewire separation which may reduce the tightness between guidewires, thereby allowing more freedom for the catheter system 5 to twist as it is delivered to the vessel bifurcation. Although the centering band is described above as being inflated hydraulically, in another embodiment of the invention the centering band may be expanded mechanically such as through a shape-memory material like nitinol. In another embodiment of the invention, the centering band is comprised of electroactive polymer material and is expanded by application of a voltage to the electroactive polymer material. Furthermore, the FIG. 9 shows a centering band 125 in the expanded state 135. In the embodiment depicted in FIG. 9, centering band 125, in fluid communication with centering band inflation lumen 130, has a conical shape with a vertex 131 and base 132. As is characteristic of a cone, the vertex 131 has a diameter less than that of the base 132. In the embodiment shown in FIG. 9, vertex 131 of centering band 125 is closer to the expandable balloon 70 than the base 132. In the embodiment shown in FIG. 10, the base 132 of centering band 125 is closer to the expandable balloon 70.

Figure 11:
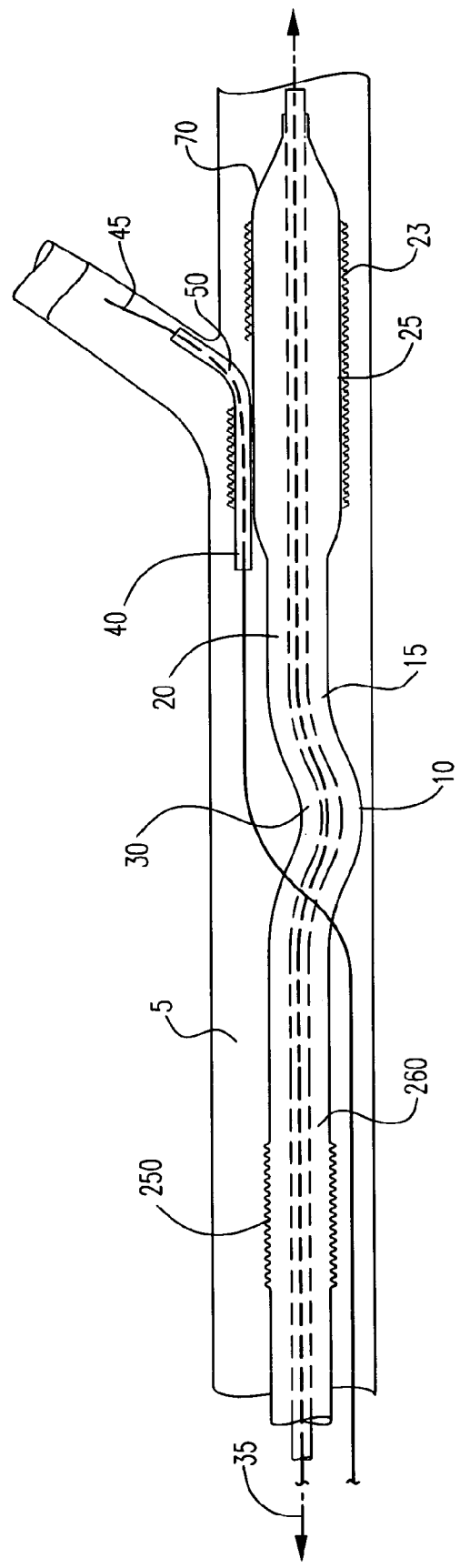
FIG. 11 is a side view of a catheter system with a catheter shaft comprising a flexible, pleated region.
Figure 12:
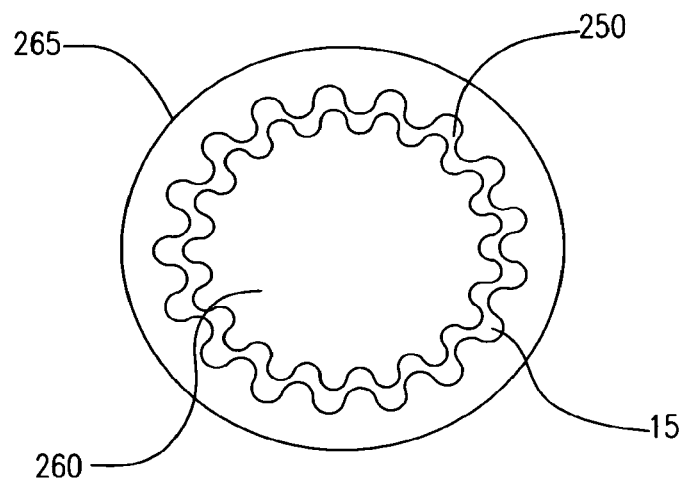
FIG. 12 is a cross-sectional view of the catheter shaft of FIG. 11 with the flexible, pleated region disposed about the entire circumference of a portion of the catheter shaft.
Figure 13:
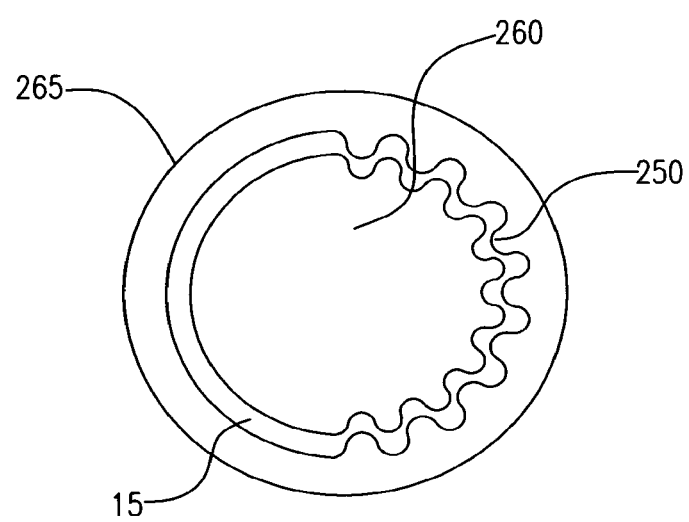
FIG. 13 is a cross-sectional view of the catheter shaft of FIG. 11 with the flexible, pleated region disposed about a section of the circumference of a portion of the catheter shaft.

The trackability of a catheter system may be improved by altering the flexibility characteristics of the catheter shaft. By making the catheter shaft more flexible in some regions than in other regions, the catheter system may be advanced through the vasculature with less difficulty, thereby potentially reducing damage to the vessel walls as well as increasing delivery accuracy. To that end, another embodiment of the invention is presented in FIGS. 11-13. FIG. 11 depicts a catheter system 5 with a catheter shaft 15 comprising a flexible, pleated region 250 about its circumference. The flexible, pleated region 250 may extend along the length of catheter shaft 15, as necessary to provide the desired flexibility. This flexible and/or soft region 250, like a bellows, will act as an area capable of twisting. Although not depicted, reinforcement may be provided underneath the flexible, pleated region 250 to sustain the inflation lumen 260. In one embodiment of the invention, the flexible, pleated region 250 extends around the entire circumference 265 of the catheter shaft 15, as shown in FIG. 12. In other embodiments, it may be desirable to have the flexible, pleated region 250 extend around only a section of the circumference 265 of catheter shaft 15.

Figure 14:
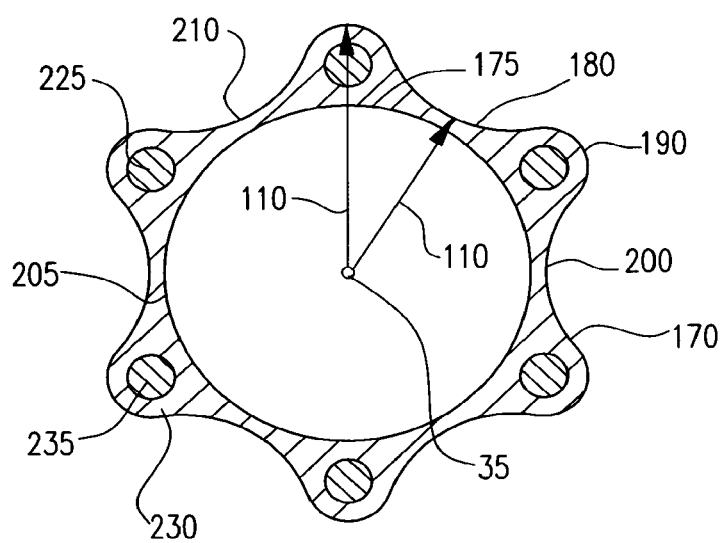
FIG. 14 is a cross-sectional view of the body of the catheter shaft of FIG. 1.

In addition to using flexible, pleated regions, altering the shape of the catheter shaft may produce similarly desirable trackability effects by aiding the catheter system's ability to twist. FIG. 14 depicts the body 170 of a catheter shaft with an interior 175, an exterior 180, and a longitudinal axis 35. Exterior 180 comprises a plurality of exterior peaks 190 and exterior troughs 200, the exterior peaks 190 being at a greater radial distance 110 from the longitudinal axis 35 of the catheter shaft than the exterior troughs 200. Each exterior peak 190 is separated by an exterior trough 200. In some embodiments, the interior 175 defines a substantially circular region 205. In some embodiments, the troughs 200 are substantially curvilinear 210. The thinner regions of the troughs may act as pivots for the guidewire, providing more twist. In order to provide more support to the catheter shaft, some embodiments of the invention include a support extending substantially parallel to the longitudinal axis 35 and through at least one peak 190 of the catheter shaft. In at least one embodiment, the body 170 is comprised of a first material 230 and the support is comprised of a different, second material 235. In some embodiments of the invention, the first material 230 is more flexible than the second material 235. In other embodiments, the first material 230 is less flexible than the second material 235.

Figure 15:
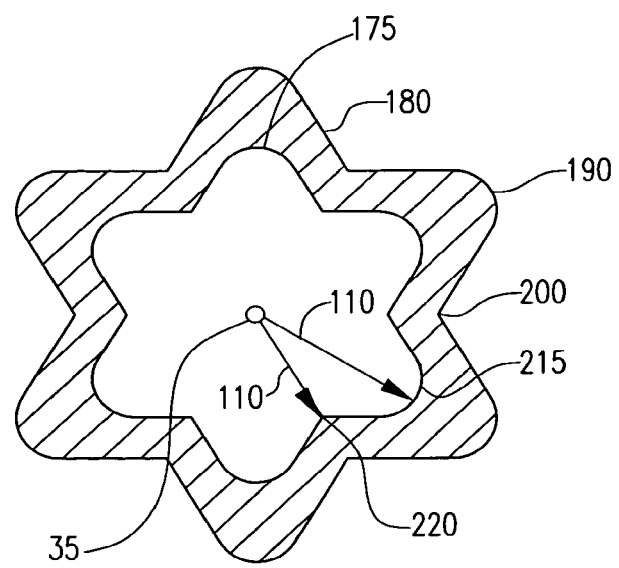
FIG. 15 is a cross-sectional view of the body of the catheter shaft of FIG. 1.

FIG. 15 depicts a variant of the embodiment depicted in FIG. 14. In FIG. 14 the interior 175 as well as the exterior 180 are comprised of a plurality of peaks and troughs. Interior peaks 215 correspond radially to exterior peaks 190, and interior troughs 220 correspond radially to exterior troughs 200. The peaks are at a greater radial distance 110 from the longitudinal axis 35 than the troughs. Each peak is separated by a trough. In some embodiments, the troughs are curvilinear (not shown).

Figure 16:
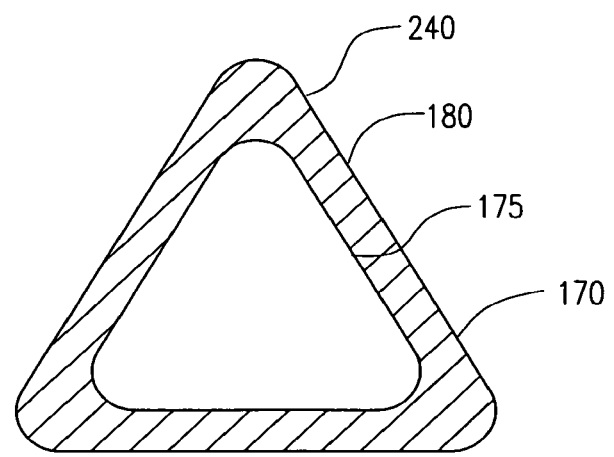
FIG. 16 is a cross-sectional view of the body of the catheter shaft of FIG. 1.

Another embodiment of the invention is shown in FIG. 16. In this embodiment, the body 170 of the catheter shaft has a substantially triangular cross-sectional shape 240. Although FIG. 16 depicts both the body interior 175 and body exterior 180 as having a triangular shape, other embodiments may have a body interior of another shape, such as substantially circular.

Trackability and/or push may be improved with the introduction of a support member extending through a catheter shaft. In the embodiment depicted in FIG. 17, catheter shaft 15 comprises a substantially tubular wall 255, and a support member 245, with first portion 270 and second portion 275. First portion 270 of support member 245 may include a flexible, pleated region 250. The flexible, pleated region 250 allows for any change in length that may occur while the catheter system 5 is twisted during delivery. In some embodiments, a section of the support member 245 is a metallic wire or wires. In at least one embodiment, at least a portion of the support member 245 is constructed of more of more polymer materials.

Figure 17:
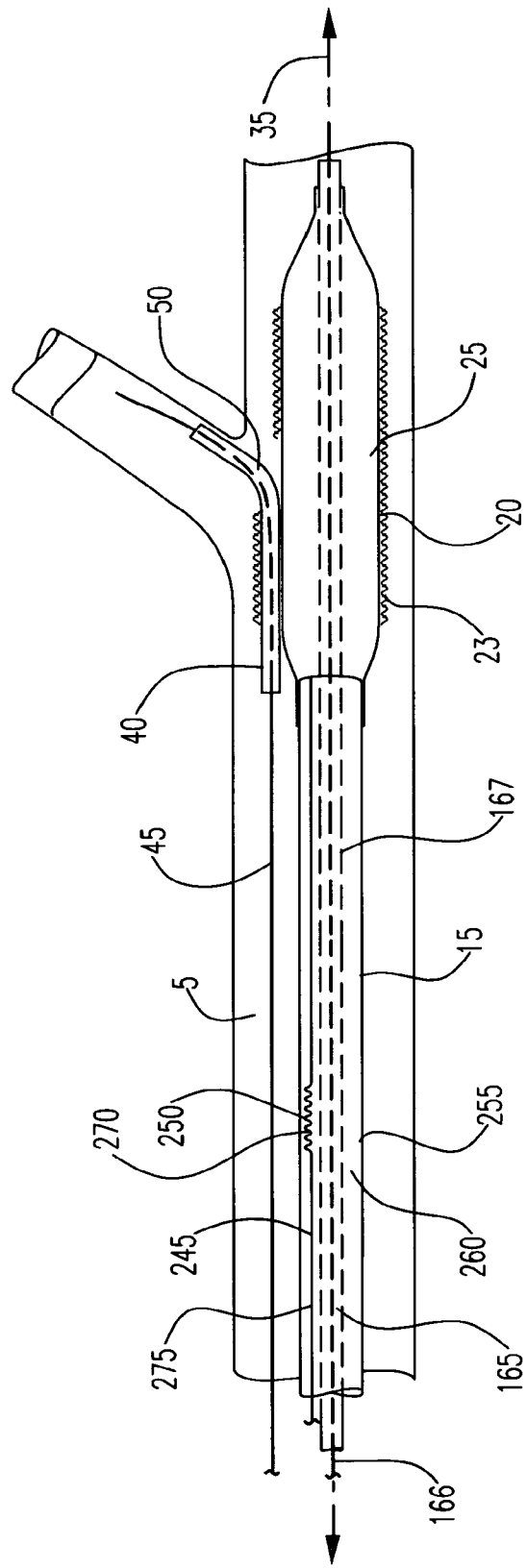
FIG. 17 is a side view of a catheter system with a support wire with a flexible, pleated region extending through the lumen of the catheter shaft.

Still referring to FIG. 17, the catheter shaft 15 defines an inflation lumen 260. In at least one embodiment, the support member 245 extends through at least a section of the inflation lumen 260. In other embodiments, the support member 245 extends through at least a section of the tubular wall 255. Although not depicted in FIG. 17, the catheter shaft 15 may further comprise a bend in the manner shown in FIG. 1.

Figure 18:
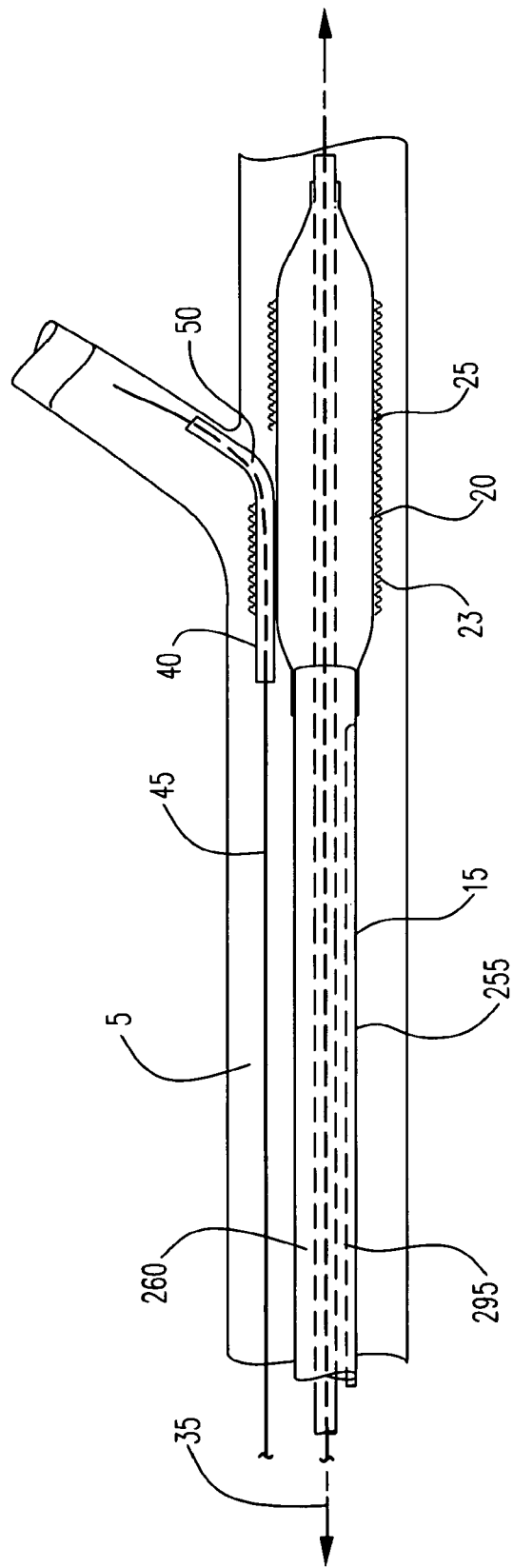
FIG. 18 is a side view of a catheter system with a push inflation lumen extending through the tubular wall of the catheter shaft.
Figure 19:
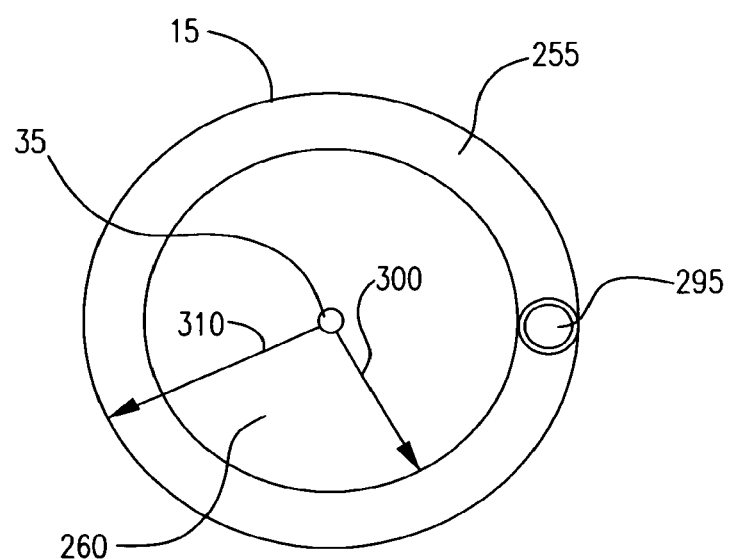
FIG. 19 is a cross-sectional view of the push inflation lumen and tubular wall of the catheter shaft shown in FIG. 18.

Push may be further improved with the addition of a push inflation lumen, as shown in FIG. 18. Having a catheter system with a flexible catheter shaft is desirable because tracking through the vessel is improved. However, the increase in flexibility may reduce push, push (i.e. stiffness) necessary to advance the catheter system through guidewire crosses. FIG. 18 depicts a push inflation lumen 295 that extends longitudinally through at least a portion of the tubular wall 255 of catheter shaft 15. The push inflation lumen is inflatable independent of the inflation lumen 260 defined by the catheter shaft 15. FIG. 19 depicts a cross-sectional view of the concept with push inflation lumen 295 extending longitudinally through the tubular wall 255 of catheter shaft 15. The tubular wall has a thickness defined by the inner diameter 300 and outer diameter 310.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A catheter system comprising:
a catheter shaft including a proximal region, a distal region and a longitudinal axis, the catheter shaft defining a primary guidewire lumen configured to receive a primary guidewire;
a balloon disposed about the distal region of the catheter shaft, the balloon having a first length; and
a side branch guidewire housing attached to the balloon, the side branch guidewire housing defining a side branch guidewire lumen, the side branch guidewire housing having a second length, wherein the second length is equal to or less than the first length of the balloon, the side branch guidewire housing comprising a first portion that extends parallel to the longitudinal axis, a bend portion, and at least a second portion that extends at an oblique angle away from the longitudinal axis and away from the balloon, wherein at least part of the first portion of the side branch guidewire housing is attached directly to the balloon, wherein the side branch guidewire housing further comprises an expandable centering band, the centering band being disposed around the second portion of the side branch guidewire housing, wherein the entire expandable centering band is spaced apart distally from the bend portion of the side branch guidewire housing, the centering band having an expanded state and an unexpanded state, wherein the first portion of the side branch guidewire housing is free from any expandable element.

2. The system of claim 1, further comprising a centering band inflation lumen in fluid communication with the centering band, the centering band adapted to receive an inflation fluid, the centering band being substantially filled with the inflation fluid in the expanded state, the centering band being substantially free of inflation fluid and substantially ring-shaped in the unexpanded state.

3. The system of claim 1, wherein the centering band inflation lumen extends adjacent to the side branch guidewire housing, the centering band inflation lumen extending proximal of the side branch guidewire housing.

4. The system of claim 1, wherein the centering band comprises a shape-memory material.

5. The system of claim 1, wherein the centering band comprises an electroactive polymer.

6. The system of claim 1, wherein the centering band in the expanded state is substantially conical, the centering band having a vertex and a base, the vertex having a diameter less than that of the base, the vertex being closer to the expandable balloon than the base.

7. The system of claim 1, wherein the centering band in the expanded state is substantially conical, the centering band having a vertex and a base, the vertex having a diameter less than that of the base, the base being closer to the expandable balloon than the vertex.

8. A catheter system comprising:
a catheter shaft defining a primary guidewire lumen configured to receive a primary guidewire;
a balloon disposed about a distal region of the catheter shaft, the balloon having a first length; and
a side branch guidewire housing attached to the balloon, the side branch guidewire housing defining a side branch guidewire lumen, the side branch guidewire housing having a second length, wherein the second length is equal to or less than the first length of the balloon, the side branch guidewire housing comprising a first portion that extends parallel to a longitudinal axis of the catheter shaft and at least a second portion that extends at an oblique angle away from the longitudinal axis and away from the balloon, wherein at least part of the first portion of the side branch guidewire housing is attached directly to the balloon, wherein the side branch guidewire housing further comprises a centering band including an inflatable portion, the centering band being disposed around the second portion of the side branch guidewire housing such that the inflatable centering band is spaced apart from the balloon, wherein the entire inflatable portion of the centering band is disposed on the second portion of the side branch guidewire housing and no inflatable portion extends onto the first portion of the side branch guidewire housing, the centering band having an expanded state and an unexpanded state.

9. The system of claim 1, further comprising a side branch guidewire, the side branch guidewire configured to extend through the side branch guidewire lumen.

10. The system of claim 1, wherein the side branch guidewire housing has a cross-sectional shape, the cross-sectional shape having a height and a width, the width being greater than the height.

11. The system of claim 1, wherein the side branch guidewire housing has a substantially elliptical cross-sectional shape.

12. The system of claim 1, wherein the side branch guidewire housing has a cross-sectional shape, the cross-sectional shape comprising a plurality of peaks and troughs, the peaks being at a greater radial distance from the longitudinal axis of the catheter shaft than the troughs, each peak being separated by a trough.

13. The system of claim 12 wherein the troughs are substantially curvilinear.

14. The system of claim 1, wherein the elongate catheter shaft proximal to the balloon has a bend portion, the bend portion comprising at least one bend bent around the longitudinal axis defining a helical path, wherein the side branch guidewire housing includes a proximal end positioned distal of the bend portion, the system further comprising a side branch guidewire configured to extend through the side branch guidewire lumen, wherein the side branch guidewire is bent around the longitudinal axis and is disposed around the elongate catheter shaft adjacent to the bend portion of the elongate catheter shaft, wherein the bend portion of the elongate catheter shaft and the bend in the side branch guidewire are configured such that when the elongate catheter shaft is advanced over the primary guidewire and the side branch guidewire, the primary and side branch guidewires may cross the elongate catheter shaft multiple times without becoming entangled.

15. The system of claim 8, further comprising a stent, wherein the balloon is configured to retain said stent thereon, and the portion of the side branch guidewire housing that extends at an oblique angle away from the balloon extends through a side branch opening in the stent.

16. The system of claim 8, further comprising a centering band inflation lumen in fluid communication with the centering band expandable portion, the centering band adapted to receive an inflation fluid, the centering band being substantially filled with the inflation fluid in the expanded state, the centering band being substantially free of inflation fluid and substantially ring-shaped in the unexpanded state.

17. The system of claim 8, wherein the centering band in the expanded state is substantially conical, the centering band having a vertex and a base, the vertex having a diameter less than that of the base, the vertex being closer to the expandable balloon than the base.

18. The system of claim 7, wherein the centering band in the expanded state is substantially conical, the centering band having a vertex and a base, the vertex having a diameter less than that of the base, the base being closer to the expandable balloon than the vertex.

* * * * *